US008189885B2

(12) United States Patent
Saha et al.

(10) Patent No.: US 8,189,885 B2
(45) Date of Patent: May 29, 2012

(54) APPARATUS AND METHOD FOR COMPUTING REGIONAL STATISTICAL DISTRIBUTION OVER A MEAN ANATOMIC SPACE

(75) Inventors: Punam Kumar Saha, Iowa City, IA (US); Milan Sonka, Coralville, IA (US)

(73) Assignee: The University of Iowa Research Foundation, Iowa City, IA (US)

( * ) Notice: Subject to any disclaimer, the term of this patent is extended or adjusted under 35 U.S.C. 154(b) by 1134 days.

(21) Appl. No.: 12/070,385

(22) Filed: Feb. 15, 2008

(65) Prior Publication Data

US 2009/0208081 A1 Aug. 20, 2009

(51) Int. Cl.
*G06K 9/00* (2006.01)
(52) U.S. Cl. ........................................ 382/128
(58) Field of Classification Search .................. 382/128, 382/131; 345/420
See application file for complete search history.

(56) References Cited

U.S. PATENT DOCUMENTS

| | | | | |
|---|---|---|---|---|
| 2005/0010106 A1* | 1/2005 | Lang et al. | .................... | 600/425 |
| 2006/0159323 A1* | 7/2006 | Sun et al. | ...................... | 382/128 |
| 2007/0081712 A1* | 4/2007 | Huang et al. | .................. | 382/128 |
| 2007/0127795 A1* | 6/2007 | Lau et al. | ...................... | 382/128 |
| 2009/0034812 A1* | 2/2009 | Nowinski et al. | ............. | 382/131 |
| 2010/0310141 A1* | 12/2010 | Wilson | .......................... | 382/131 |

OTHER PUBLICATIONS

Cootes et al, "The Use of Active Shape Models for Locating Structures in Medical Images", Image and Vision Computing, vol. 12, No. 6, Jul. 1994, pp. 355-366.*
Prastawa et al, "Automatic Segmentation of MRI Images of the Developing Newborn Brain", Medical Image Analysis 9 (2005), pp. 457-466.*
Saha, P.K.; Zhang, H.; Sonka, M.; Christensen, G.E. and Rajapakse, C.S., 2007. Active Index Model: A unique Approach for Regional Quantitative Morphometry in Longitudinal and Cross-Sectional Studies. *Medical Imaging 2007: Image Processing*, edited by Josien P. W. Pluim, Joseph M. Reinhardt, Proc. of SPIE vol. 6512, 65121B.
Prastawa, Marcel; Gilmore, John H.; Lin, Weili and Gerig, Guido, 2005. Automatic segmentation of MR images of the developing newborn brain. *Medical Image Analysis 9*, 457-466.
Timp, Sheila and Karssemeijer, Nico, 2006. Interval change analysis to improve computer aided detection in mammography. *Medical Image Analysis 10*, 82-95.
Naish, Josephine H.; Parker, Geoffrey J.M.; Beatty, Paul C.; Jackson, Alan; Waterton; John C.; Young Simon S. and Taylor, Chris 2004. Improved Regional Analysis of Oxygen-Enhanced Lung MR Imaging Using Image Registration. *MICCAI 2004, LNCS 3216*, pp. 862-869, C. Barillot, D.R. Haynor and P. Hellier (Eds.).

* cited by examiner

*Primary Examiner* — Jack Berman
*Assistant Examiner* — David E Smith
(74) *Attorney, Agent, or Firm* — Valauskas Corder LLC

(57) ABSTRACT

The present invention is an apparatus and method for computing regional statistical distributions or characteristics of one or more quantitative measures over a mean anatomic space for one or more predefined populations and uses this statistical distributions/characteristics to study, research or understand the regional response of a disease or a treatment process and to regionally assess clinical status in patient data from an unknown population for diagnostic purposes.

21 Claims, 11 Drawing Sheets

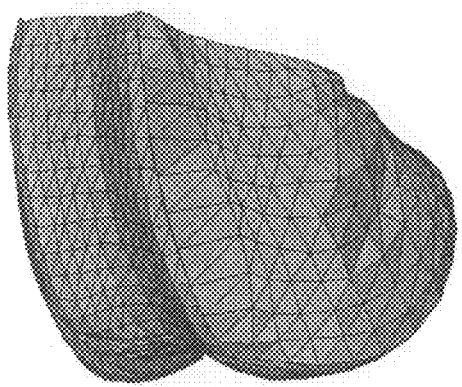
FIG. 6A
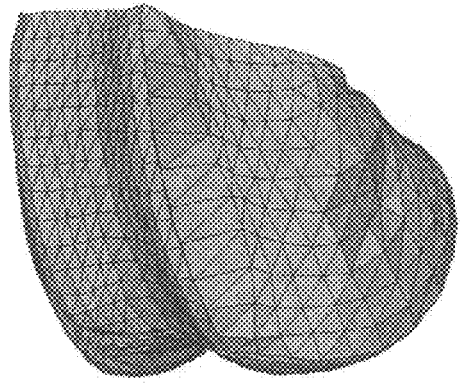
FIG. 6B-I
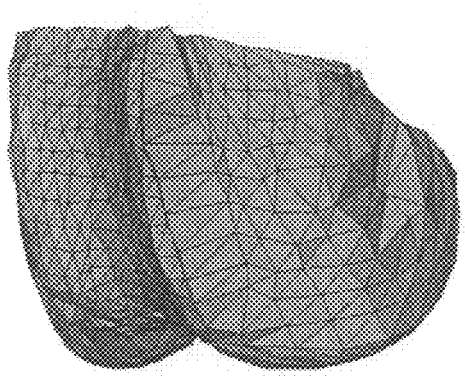
FIG. 6B-II
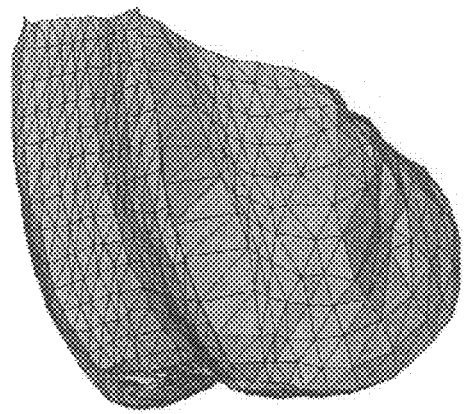
FIG. 6B-III

APPARATUS AND METHOD FOR COMPUTING REGIONAL STATISTICAL DISTRIBUTION OVER A MEAN ANATOMIC SPACE

FIELD OF THE INVENTION

The present invention relates generally to quantitative medical image analysis and understanding regional responses of a disease or treatment. More particularly, the present invention relates to a method and apparatus for computing regional statistical distribution of at least one quantitative measure over a mean anatomic space for a plurality of clinically defined populations for the purpose of understanding regional response of a disease or treatment for diagnostic purposes.

BACKGROUND OF THE INVENTION

Currently, medical imaging methods generally analyze global changes in quantitative measures in response to a disease or treatment. A major disadvantage of these methods is that the effects of the measured disease/treatment get diluted due to global averaging and therefore, lose their strength for early detection. Recent advancements in digital medical imaging have opened avenues for quantitative analyses of different volumetric and morphometric indices in response to a disease or a treatment.

Although three dimensional (3D) anatomic atlas models exist, they are primarily for human brain imaging. The focus is to segment the different anatomic regions of interest (ROI) in a given human brain data and statistical analysis of the transformation to characterize different populations.

Alternatively, bone-related research works have studied disease or treatment induced regional structural changes. A longitudinal study of the effect of salmon calcitonin on trabecular bone (TB) architecture observed large regional variations in statistical significance for distinguishing remodeling changes in trabecular architecture due to treatment.

In a study involving 39 vertebral fracture and 70 age-matched control subjects, all post-menopausal women, it was demonstrated that radiography-based TB anisotropy parameters distinguished between fracture and control groups, showing further that different regions in the calcaneus had different statistical significance.

Further, peripheral quantitative computed tomography (pQCT) and micro-computed tomography ($\mu$CT) images of human cadaveric TB samples from the anterior/posterior and superior/inferior regions of the ultra-distal tibia and mid-femur neck, respectively, demonstrated regional differences in both BMD and micro-architectural parameters.

Recently, strong orientation differences were observed between the medial and lateral sides of axial cross sections in $\mu$MRI images of the human distal radius. Regional analysis of TB micro-architecture has also been found to distinguish between osteoarthritic and non-osteoarthritic women.

Accordingly, a major challenge in performing such analysis is the lack of technology for building a mean anatomic space (MAS) that allows analyzing data from a given subject in reference to an anatomic coordinate system. Such a system would provide an effective tool for point-by-point regional analysis and comparison of quantitative indices for data coming from a longitudinal or transverse study. Using an anatomic coordinate system would open several avenues for quantitative data analysis.

As an example, at the training phase, the computation of regional distributions of quantitative parameter(s) from two or more known populations (e.g., normal and different diseased groups) would be immediately ready for diagnostic purpose in a subject whose clinical status is unknown. Such a system would be useful for both cross sectional and longitudinal studies and for early diagnostic, and would be a vital tool for understanding regional response of a disease or treatment at various stages of its progression.

SUMMARY OF THE INVENTION

The present invention solves the shortcomings described above. The invention, also known as the Active Index Model (AIM), consists of apparatus and method to compute regional statistical distributions or characteristics of one or more quantitative measures over a mean anatomic space for one or more predefined populations and uses this statistical distributions/characteristics to study, research or understand the regional response of a disease or a treatment process and to regionally assess clinical status in patient data from an unknown population for diagnostic purposes.

The present invention provides a point-by-point comparison of different parameters from one or multiple predefined clinical populations, and is useful for both cross sectional and longitudinal studies and early detection of disease and treatment response. The present invention comprises a method for detecting regional physiological differences and/or changes in an anatomical structure, for example, bone density over the femur.

The first step of the AIM process is to graphically (or, by some other means such as automatic landmark detection, etc.) delineate the landmarks of an anatomical structure in each training dataset and to combine the landmark data from different datasets creating a mean anatomic space (MAS) into which patient data can be mapped. This delineation is a one-time manual/semi-manual/automatic step on a training dataset for a given anatomical structure. The next step is the gathering of a one or multiple spatially distributed quantitative measure(s) for each dataset from a given population (for example, a healthy individual versus a diseased individual), and then mapping the measures on to the MAS. This step map may be accomplished by first mapping each dataset on the MAS and then gathering the spatially distributed measures. Once the spatial measures are mapped on the MAS, the information can be used in various ways to study and diagnose pathological conditions.

In step one of the training phase; the various anatomical landmarks are manually/semi-manually/automatically entered, for example, the various joints of a hand on some datasets to build a statistical model of the shape. The step one of the training phase ends and the system can then use this exemplary "mean hand" and the statistical shape model to automatically aggregate imaging data from hundreds of hands with different sizes that have the same identifiable anatomical landmarks, such as, the joints, knuckles, etc.

The second step of AIM's training process then involves using the regional quantitative measure of data from the training and aggregation phases mapped onto the MAS. These anatomically registered measures at any location on the MAS for a specific population are then combined into a statistical distribution. These regional distributions over the MAS from different population are subjected in various types of analysis and comparisons. These comparisons can be between a healthy population and a diseased population (transverse), a healthy population a diseased population and an unknown individual (transverse), a healthy and multiple diseased populations (transverse), or the same individual over a period of time (longitudinal), among other comparisons.

The present invention is an improvement over the current technology because it provides a more accurate characterization of disease conditions by quantifying point-by-point region-specific differences of an anatomical structure between two or more populations, for example, a healthy population versus a diseased population. The AIM process provides earlier and more accurate diagnosis by comparing a patient's region-specific information with that of known populations. Further, the AIM process generates more accurate tracking of progression of a disease and/or treatment that has non-uniform regional manifestations.

Additionally, the present invention is not limited to static images, and is thus extremely useful to compare motion, for example, of specific regions of the heart between populations. The present invention is also not limited to measuring one quantitative measure, and can be used to study multiple quantitative measures of a region simultaneously. Further, the AIM system does not require new imaging techniques, and can utilize existing imaging data, with the ability to incorporate future imaging technology as it becomes available.

The present invention allows for the creation of MAS for a particular region of the body as described herein. The creation of the particular MAS can be done once and used repeatedly, or it may be revised in the future. The particular MAS is stored in a database, either locally or remotely, with other MAS of various regions of the body for future use. The MAS can then be accessed and mapped with historical data from a specific population that is also stored either locally or remotely.

Once the MAS of a body region has been computed, the data from any particular subject or patient from a relevant population can be mapped and compared to the historical data for that particular body region. This method computes regional statistical characteristics for all relevant populations over the MAS. These regional statistical characteristics can be used to regionally assess clinical status of a patient from an unknown population. Also, these regional characteristics can be used to study/research/understand the regional manifestation/response of a disease or treatment process at different stages of progression.

In accordance with an object of the present invention, the MAS and historical data is stored in a remote database, and a doctor or medical facility can subscribe to access a particular MAS, and map its own data, or utilize historical data that has been previously mapped for that MAS. The doctor or medical facility can then use this MAS map to compare and study its patients for the particular anatomic structure.

Another object of the present invention is to provide the software necessary for the doctor or facility to generate its own MAS for particular regions and incorporate its own historical data for comparison and study of its patients. In this embodiment, the doctor or hospital can also receive historical data pertaining to each MAS.

Further aspects of the invention will become apparent from consideration of the drawings and the ensuing description of preferred embodiments of the invention. The embodiments described below are in specific reference to surface-AIM and volume-AIM, although a person skilled in the art will realize that other computational frameworks are possible and that the details of the invention can be modified in a number of respects, all without departing from the inventive concept. Thus, the following drawings and description are to be regarded as illustrative in nature and not restrictive.

BRIEF DESCRIPTION OF THE DRAWINGS

FIGS. 6A-6B are images generated in accordance with the present invention;

DETAILED DESCRIPTION OF THE PREFERRED EMBODIMENT

The present invention, a novel computation framework known as Active Index Model (AIM), is used for solving the problems of analyzing regional implications of different quantitative parameters in longitudinal or cross-sectional studies.

Figure 1:
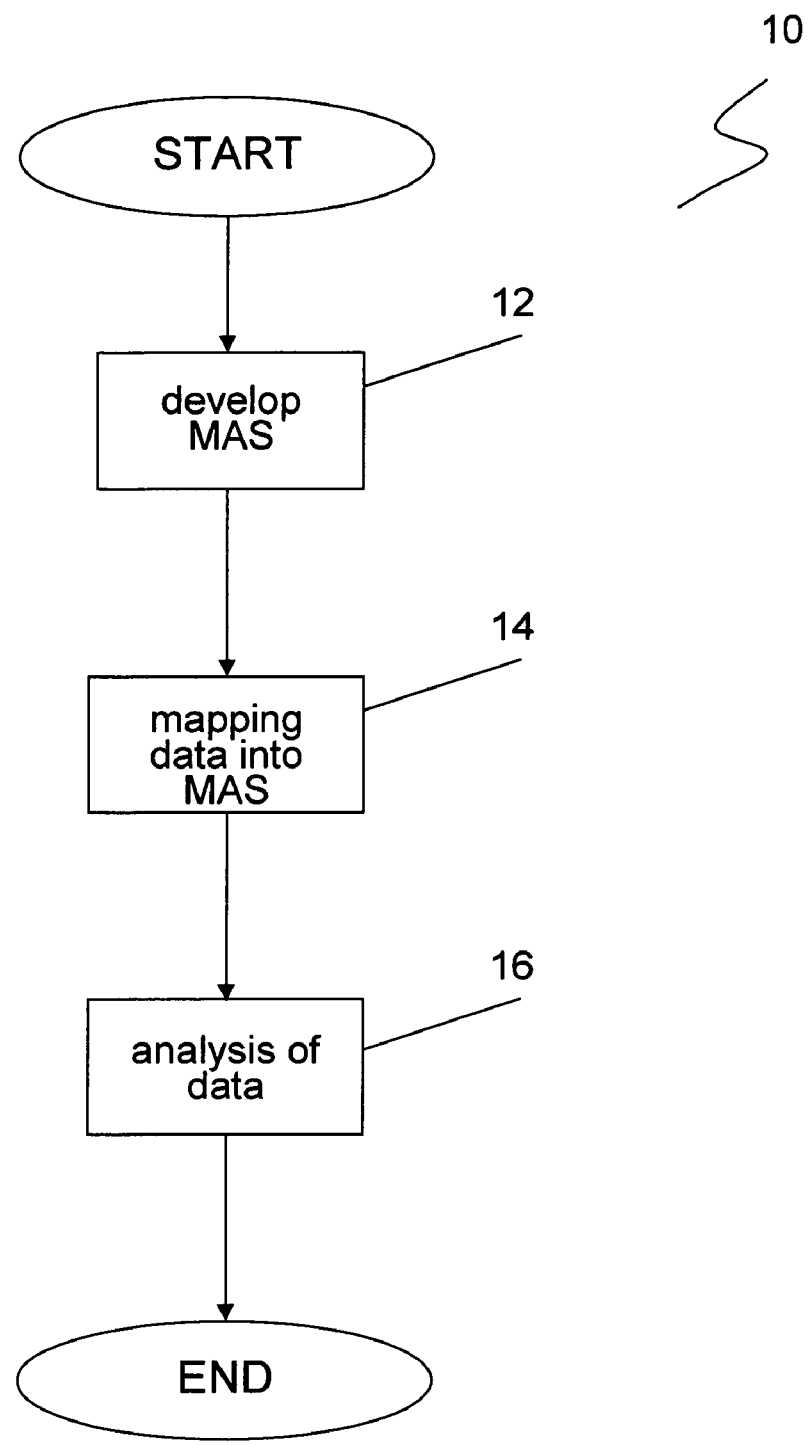
FIG. 1 is a flow chart of one embodiment of a method for creating an Active Index Model according to the present invention.

As shown in FIG. 1, the present invention, AIM 10, consists of three steps: (1) developing a mean anatomic space (MAS) for a particular anatomic site 12, (2) mapping specific information or data into the MAS 14, and (3) performing regional statistical analysis of quantitative measures from different populations to assist in assessing regional response to a disease or treatment progression 16 and to use this regional statistical distributions to rate a disease/treatment status of patient from her/his image data after mapping the data onto the MAS.

The primary objective of the present invention is to develop a method for regional analyses of quantitative indices over a specific body region for data from different populations (in cross-sectional studies) and/or time points (in longitudinal studies) 16. This objective is fulfilled by developing a mean anatomic space 12 for a given body location or anatomic structure from a set of training data and then it is solved by applying an active shape model (ASM).

Specifically, ASM generates a set of ordered sets of landmarks that are used to build regional correspondences in AIM. Although, the method is equally applicable in any dimension, the preferred embodiment utilizes a three dimensional (3D) model.

Figure 2:
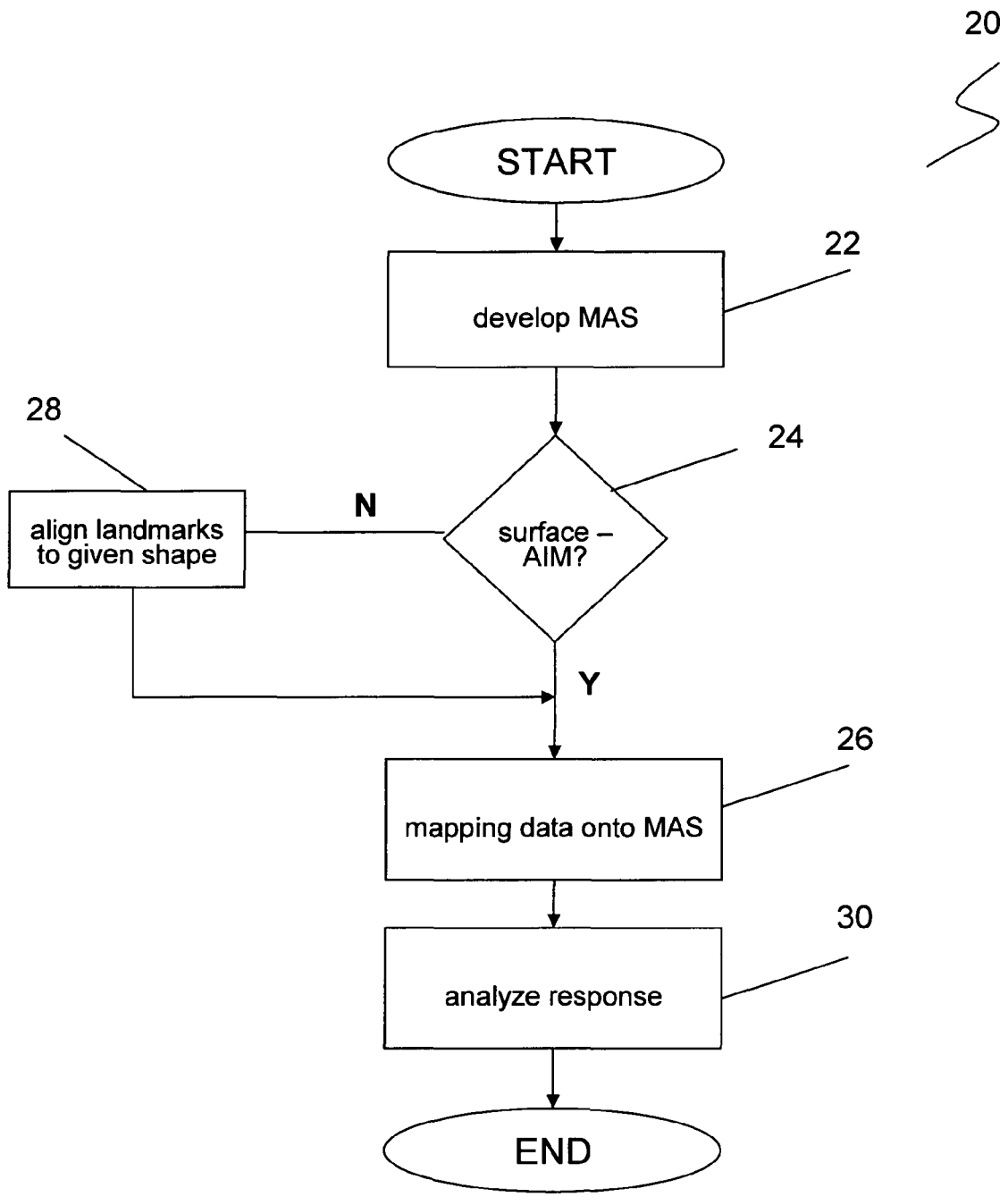
FIG. 2 is a flow chart of one embodiment of a method for creating an Active Index Model according to the present invention.

FIG. 2 shows the 3D model 20, in which there are two distinct cases: (1) quantitative indices are computed over the surface of the target body region (surface-AIM), and (2) quantitative indices are computed over the volume of the target body region (volume-AIM).

Examples of surface-AIM cases include, but are not limited to, cardiac deformations, optics, cartilage thickness over femur surface, etc. Examples of volume-AIM cases include, but are not limited to, bone density and structural distribution at different anatomic sites, pulmonary ventilation, cartilage, etc. One having ordinary skill in the art would understand that these two different cases, surface-AIM and volume-AIM could be applied to any anatomical structure in the body.

The building blocks of AIM are somewhat different for these two cases. In both the surface-AIM and volume-AIM cases, the MAS is computed 22 as the mean shape derived from ASM, and the same ASM is used to segment the target region (shape) for a given data set. In surface-AIM 24, the regional mapping of the specific shape onto MAS 26 is directly obtained from the correspondence of the ASM landmarks as they are generally distributed over the surface of the shape. However, a separate step is needed to build the mapping of the shape volume (volume-AIM) onto the MAS 28. Although there are a number of methods available, the preferred embodiment utilizes the free-form deformation computed by applying the landmark-based thin-plate spline (TPS) method so that the ordered set of landmarks in the given shape is aligned to the MAS 28.

The third building block of AIM is to analyze the regional response 30 of one or more indices to a disease or treatment progression.

Figure 3:
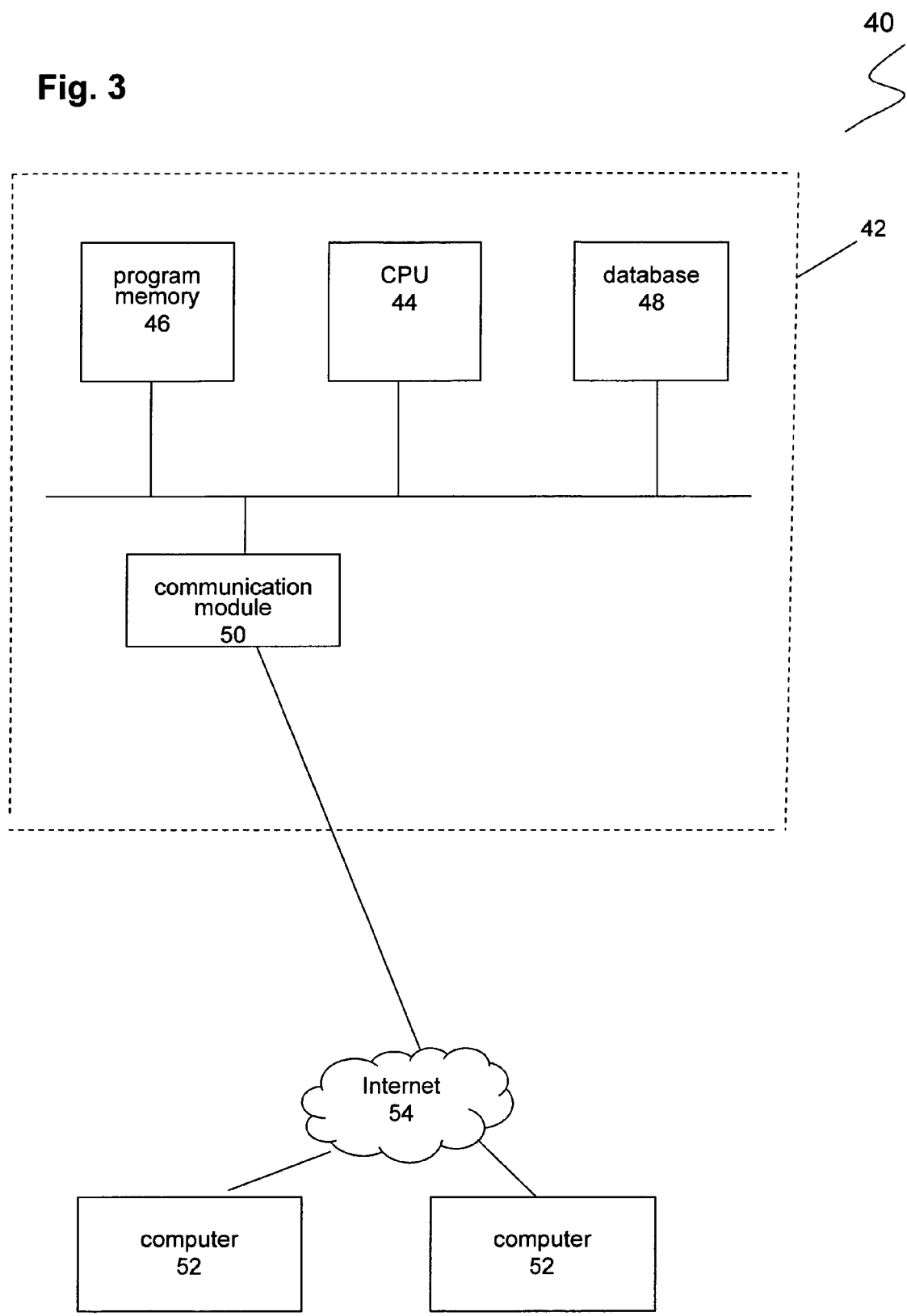
FIG. 3 is a schematic diagram illustrating one embodiment of an Active Index Model for implementing the present invention.

FIG. 3 shows the system 40 of the present invention which allows for the creation of MAS for one or more specific regions of the body as described herein. The system 40 is comprised of a server 42 which includes, among other items, a CPU 44, program memory 46 at least one database 48 and a communication module 50. The server 42 can communicate with remote computers 52 through the Internet 54. Other communication vehicles can be used, such as a proprietary Intranet, etc. without departing from the scope of the invention.

Further, the server 42 can be used as a stand alone system to accomplish the aspects of the present invention as described below. Also, each computer 52 can also be equipped with the necessary software and/or data to practice the invention in a stand alone mode, i.e., without the necessity of obtaining software and/or data from a server. Of course, each of the server 42 and remote computer 52 can perform some or all of the aspects of the present invention, alone or together.

As a non-limiting example, each developed MAS may be stored on the database 48 of the server 42 along with historical data from one or more populations. The particular patient data that will be mapped onto the MAS may be stored on the remote computer 52 at, for example, the doctor's office. Accordingly, the data stored on the remote computer 52 can be uploaded to the database 48 on the server 42 for comparison to a given population with the results returned to the remote computer 52.

The creation of each particular MAS can be done once and used repeatedly, or it may be revised based on additional information received in the future. The MAS, regardless of where it is stored, can then be accessed and mapped with historical data from a specific population that is also stored locally or remotely.

In the preferred embodiment, each MAS and the related historical data for the various populations is stored in the database 48 on the server 42. Any doctor or medical facility wishing to access the MAS and historical data can subscribe to a service that allows access through the Internet 54 to the server 42, the database 48, and the one or more MAS and related population data residing on the database 48. The access may be unlimited for research purposes, or may be limited to the doctor's specialty. The doctor or medical facility can then use the MAS to map a particular patient's data to compare to the historical data.

Additionally, the software necessary for the doctor or medical facility to generate its own MAS for particular regions and incorporate its own historical data for comparison and study of its patients can be sold as a turnkey unit to the doctor or facility. The doctor or medical facility may also receive historical data updates from time to time pertaining to the historical data for the one or more MAS.

As described herein, the ASM and TPS methods are useful for the first step in building an AIM. In the ASM method, an object is described by an ordered set of n points, referred to as landmark points. A set of landmark points is specified for each of the s training images. From these collections of landmark points, a point distribution model is constructed. For any given training image, a shape vector x is constructed from the specified landmark points $(x_1, y_1, z_1), \ldots, ((x_n, y_n, z_n)$ as follows $$x = (x_1, y_1, z_1 \ldots, x_n, y_n, z_n)^T. \tag{1}$$

Principal component analysis (PCA) is applied to shape vectors computing the mean shape $\bar{x}$ and covariance matrix $\Sigma$ $$\bar{x} = \frac{1}{s}\sum_{i=1}^{s} x_i, \text{ and } \Sigma = \frac{1}{s-1}\sum_{i=1}^{s}(x_i - \bar{x})(x_i - \bar{x})^T, \tag{2}$$

and the eigensystem of the covariance matrix $\Sigma$. The eigenvectors $\phi_1, \phi_1, \ldots, \phi_t$ corresponding to the t largest eigenvalues $\lambda_1, \lambda_2, \ldots \lambda_t$ are retained in a matrix $\Phi = (\phi_1 | \phi_2 | \ldots | \phi_t)$. A shape can now be approximated by $$x \approx \bar{x} + \Phi b \tag{3}$$

where b is a vector of t elements containing the model parameters, computed by $$b = \Phi^T(x - \bar{x}) \tag{4}$$

When fitting the model to a set of points, the values of b are constrained to lie within the range $\pm m\sqrt{\lambda_i}$, where m usually has a value between two and three. The number t of eigenvalues to retain is chosen so as to explain a certain proportion $f_v$ of the variance in the training shapes, usually ranging from 90% to 99.5%. The desired number of modes is given by the smallest t for which $$\sum_{i=1}^{t} \lambda_i \geq f_v \sum_{i=1}^{2n} \lambda_i. \tag{5}$$

The landmark-based TPS image registration algorithm can be used to register the template image $C_T$ with the target image $C_S$. by matching corresponding landmarks identified in both images. This method provides registration at non-landmark points by interpolation such that the overall transformation smoothly maps the template into the shape of the target image. If $q_i$ and $p_i$ for i=1, 2, ..., m, denote the m corresponding landmarks in the template $C_T$ and target $C_S$ images, respectively, and C denotes the domain of both the template image $C_T$ and target image $C_S$, then the forward transformation h:C→C is defined as the mapping that transforms $C_T$ into the shape of $C_S$ and the forward displacement field is defined as u(x)=h(x)−x.

The landmark image registration problem can be thought of as a Dirichlet problem and can be stated mathematically as finding the displacement field u that minimizes the cost function $$\text{Cost} = \int_C \|Lu(x)\|^2 dx \quad (6)$$

subject to the constraints that $u(p_i)=q_i-p_i$ for $i=1, 2, \ldots, m$. The operator L denotes a symmetric linear differential operator and is used to interpolate the displacement field u between the corresponding landmarks. When $L=\nabla^2$, the problem reduces to the thin-plate spline image registration problem where $\nabla^2$ is the Laplacian operator. It is well known that the TPS displacement field u(x) that minimizes the bending energy defined by Equation (6) above has the form $$u(x) = \sum_{i=1}^{M} \xi_i \phi(x - p_i) + Ax + b. \quad (7)$$

The matrix A and the vector b define an affine transformation and the interpolant function used for this work was $\phi(r) = r^2 \log r$. The values of A and b were determined using least squares estimation. Next, the unknown vectors $\xi_i$ were determined by substituting the constraints $u(p_i)=q_i-p_i$ for $i=1, 2, \ldots, m$ into Equation (7) and solving the resulting set of equations.

AIM Trial Applications

The present invention described herein was applied to two clinically relevant applications. Specifically, the AIM method of the present invention was applied for analyzing regional trabecular bone (TB) structural distribution, in this case in rabbit femur using data from μCT imaging and to localize the affected myocardial regions from cardiac MR data. Assessment of the quality of structural arrangement of trabecular bone is useful for early diagnosing of several skeletal diseases including osteoporosis and osteoarthritis. Recent advances in bone magnetic resonance imaging (MRI) offer an opportunity to resolve trabeculae in images acquired in vivo.

Various topological and geometric properties of TB networks for characterizing TB architecture have been reported in the literature and the application used parameters derived from digital topological analysis (DTA) for quantifying TB architecture which has been applied in several research and clinical studies.

Additionally, the present invention is applied to a ventricular function analysis, which is essential for the disease characterization and progression identification of the Tetralogy of Fallot (TOF), which results in a lack of blood flows to the lungs to supply the body with oxygen. The Tetralogy of Fallot has four components: (1) a ventricular septal defect or a large hole between the two ventricles allowing venous blood to pass from the right to left ventricle; (2) stenosis, or a narrowing at, or just beneath, the pulmonary valve, blocking the flow of venous blood into the lungs; (3) a more muscular right ventricle than is normal; and (4) an aorta that lies directly over the ventricular septal defect.

The derived functional indices are often used to determine whether further surgical treatment is required. Conventional ventricular function indices of end-diastolic volume, end-systolic volume, and ejection fraction are derived from 2D manual tracings performed on short axis magnetic resonance (MR) image data. The accuracy and reproducibility of such volumetric indices are affected by both imaging and human factors such as non-cubic voxel size, incomplete ventricular coverage, respiratory motion, or inter- and intra-observer variability of manual tracing. In addition, the indices contain only a very limited number of cross-sectional slices and also incomplete temporal information and therefore cannot fully describe the four-dimensional (4D, 3D+ time) nature of the cardiac motion.

Consequently, the indices represent a very limited set of cardiac function descriptors. Further and maybe most importantly, these indices are global and do not describe local properties of the myocardium. As described herein, the locality of the functional assessment is critical to administration of proper treatment as well as to obtaining correct diagnosis, for example, with respect to local cardiac wall motion or myocardial viability.

In order to demonstrate the effectiveness of surface-AIM and volume-AIM, the data from cardiac MR and micro-CT bone applications is incorporated. The methods adopted for each of these two applications are discussed below.

AIM for Cardiac MR Imaging

This application incorporates 3D ASM data at two time points; end-diastole and end-systole, from a previous 4D cardiac MR study. Using this data provides for the analysis of the ASM data using the AIM method.

Model Building: Setting Landmarks, Training, and Segmentation

The shape of the ventricular surface can be expressed by triangular mesh whose vertices are considered landmarks. The landmarks also provide a reference frame on which the correspondence between voxels inside the ventricular surface can be defined. This application uses a template-based approach, automated shape vector construction, to automatically create shape landmarks and their correspondences. The automatic landmark scheme is designed to achieve two goals: (1) represent sample shapes using the same number of landmarks, and (2) achieve good correspondence of landmarks.

The first goal is achieved by using the landmark template. To satisfy the second goal, the displacements of landmarks must be as small as possible. This is accomplished by using a 3D implementation of the automatic landmark and treating the ventricular surface of each cardiac phase as a 3D sample shape.

The construction of 4D shape and texture vectors can subsequently be obtained by a simple vector concatenation process. With 4D shape and texture samples available from manual tracing and represented in the 4D space, the construction and training of a 4D Active Appearance Model (AAM) is obtained following the standard procedure. The 4D AAM segmentation follows the usual iterative model matching approach.

Analysis of Regional Cardiac Deformation Using AIM

The application uses the 3D cardiac ASM data of the epicardium surface of the right ventricle at systole and diastole. A total of 402 landmarks are used to represent the epicardium surface, and a mesh was created from these landmarks by assigning an adjacency relation (FIG. 8). Allowing $d_1$, $d_2, \ldots d_{201}$ to denote the landmark locations at diastole and allowing $s_1, s_2, \ldots, s_{201}$ to denote the matching landmarks of the same subject at systole. The landmarks are registered using Procrustes analysis and a deformation vector $\delta_i$ for the ith landmark is computed as $d_i-s_i$. A smooth deformation field is computed over a second order neighborhood as follows:

$$\delta_s(i) = \frac{\delta(i) + w_1 \sum_{j \in N(i)} \delta(j) + w_2 \sum_{j \in N(i)} \sum_{\substack{k \in N(j) \\ k \notin N(i)}} \delta(k)}{1 + \sum_{j \in N(i)} w_1 + w_2 \sum_{j \in N(i)} \sum_{\substack{k \in N(j) \\ k \notin N(i)}} w_2} \quad (8)$$

Then, the scalar value of the magnitude of the smooth deformation at each landmark location for 25 control and 25 patient subjects are analyzed using an unpaired t-test.

AIM for Rabbit Femur Micro-CT Imaging

The methods for regional analysis of TB architectural indices in a rabbit femur bone using μCT imaging are described herein. For this purpose, the trial application used sham-treated rabbit femur μCT data. A group of 9 animals underwent sham surgeries and were used as controls. For the trial application, only the data from the control group were used. All images were acquired and reconstructed at isotropic 32.5 μm resolution. In order to test the potential viability of the methods in in-vivo studies, digital images were down-sampled to a resolution of 165 microns prior to analyses.

Model Building: Landmarking, Training, and Segmentation

Pre-Processing

Figure 4C:
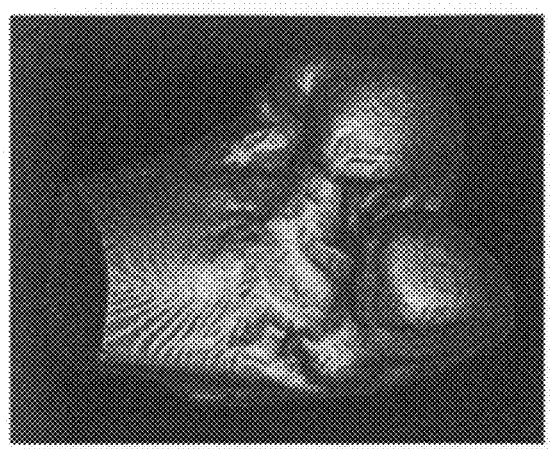
FIGS. 4A-4C are images generated in accordance with the present invention.
Figure 4B:
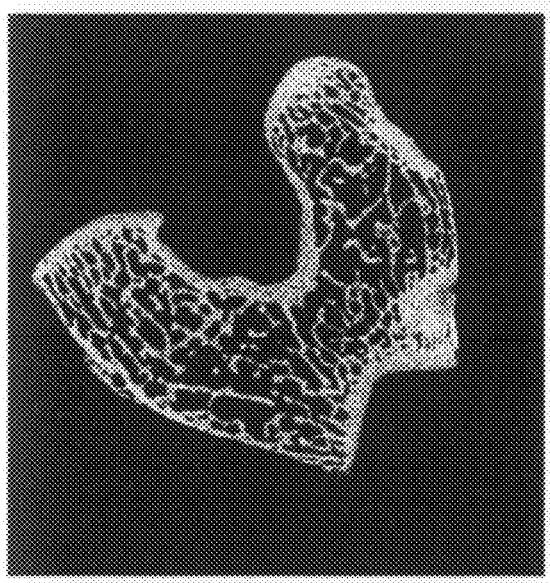
Figure 4A:
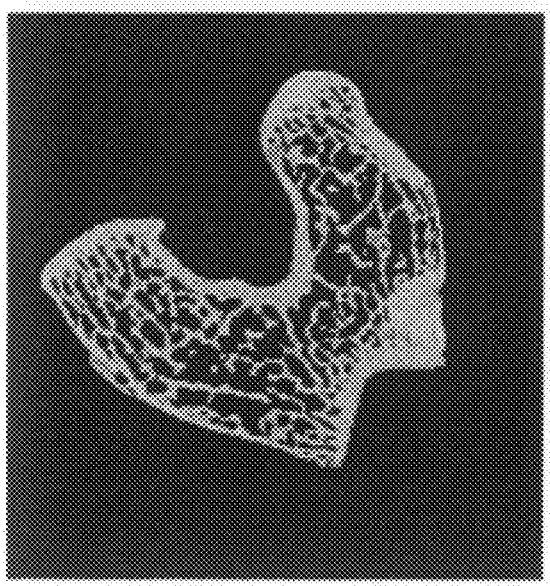

FIGS. 4A and 4B show image slices from an original μCT image of a sham-treated rabbit femur acquired at 33 μm isotropic resolution. FIG. 4B is the image slice matched to that of 4A after down-sampling, thresholding, and 26-connectivity analysis. FIG. 4C shows a surface rendered display of the femur after filling marrow space with bone.

The raw μCT images (an image slice is shown in FIG. 1A) are processed through several steps to compute the 3D femur volume region after fusing the marrow space with bone (FIG. 1C) for landmark generation. This task is accomplished in several steps.

First, the bone region is interactively thresholded using a Matlab-based graphical user interface. A binary 26-connectivity analysis is applied on the threshold image and the largest connected component is considered as the bone region (FIG. 1B). The separation between the marrow space and the background is obtained by using a morphological closing operation with a ball of diameter 5 voxels filling the vessel pathways through cortical bone entering into bone marrow. A surface rendered view of the combined bone and marrow space is illustrated in FIG. 1C. This 3D femur region is used to construct an ASM of the rabbit femur.

Landmark Generation

New landmark generation can be accomplished by manually identifying a fewer fiducial landmarks on a given 3D object, and then automatically generating the rest of secondary landmarks with reference to the fiducial ones.

Figure 5C:
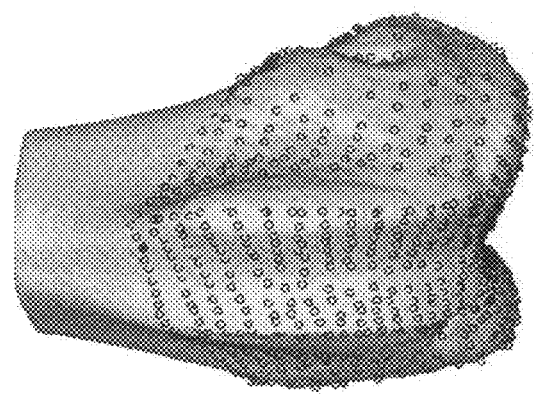
FIGS. 5A-5C are images generated in accordance with the present invention.
Figure 5B:
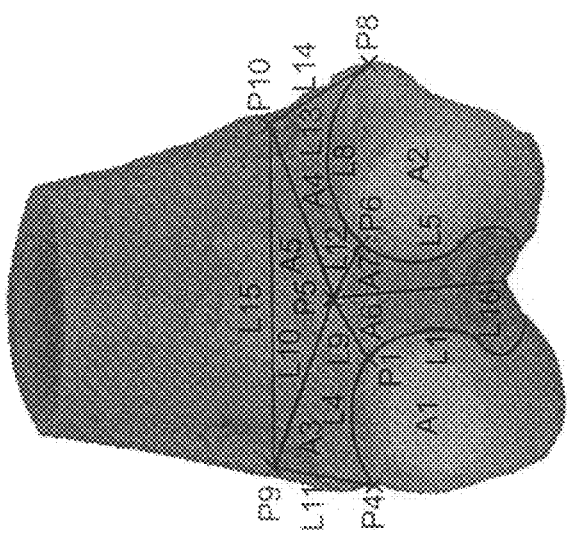
Figure 5A:
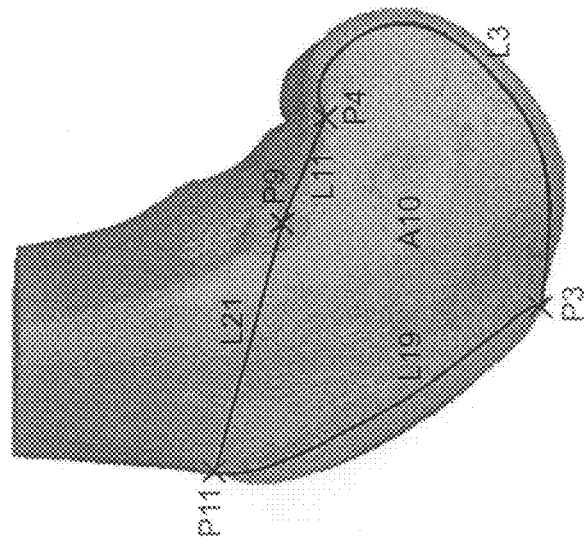

FIG. 5A shows the landmarks on a rabbit femur surface. FIG. 5B indicates the different fiducial landmark lines, areas, and points on the rabbit femur, and FIG. 5C shows the secondary landmark generated using the reference of fiducial landmarks.

A few fiducial landmarks with precise anatomic definition are located on the femur surface using a Matlab-based graphical user interface tool. Instead of point-landmarks, common anatomic curves on rabbit femurs are chosen and each labeled as a specific fiducial landmark. All together 22 lines, denoted by $L_i | 1 \leq i \leq 22$, have been defined on the femur, partitioning its outer surface into eleven areas, denoted by $A_i | 1 \leq i \leq 11$. Each of the points labeled by $P_i | 1 \leq i \leq 12$ denotes an end point to one or more fiducial landmark line. See FIG. 5 for illustrations of several fiducial landmarks.

The following describes the steps for generating an individual fiducial landmark line $L_i$. The line $L_i$ is drawn on a femur surface S by manually depositing a sequence of points, i.e., $Q = (q_1, q_2, \ldots, q_l)$. From this sequence of user-specified points, a smooth curve, essentially the fiducial landmark line $L_i$, is generated on S by iteratively using the following steps:

Step 1: Compute a $2^{nd}$ order B-spline π from the sequence of points Q.

Step 2: Generate a new sequence of points from π and S as follows:

Step 2a: Uniformly sample π generating a new sequence of points $Q' = (q'_1, q'_2, \ldots, q'_l)$.

Step 2b: Project Q' on S by replacing each of $q'_i$ with its closest point $q''_i$ on S.

Step 3: Repeat Step 1 with $Q = (q''_1, q''_2, \ldots, q''_l)$

Once all line landmarks $L_i | 1 \leq i \leq 22$ are generated, an ordered set of secondary landmarks (FIG. 5B) is generated on each of the eleven areas $A_i | 1 \leq i \leq 11$ by uniformly selecting points on Ai and then projecting them on the femur surface S using a similar method as above. Unlike fiducial landmarks, each secondary landmark is a point. Secondary landmarks are distributed on each area Ai according to a pre-determined pattern and also, on each fiducial landmark line Li at a pre-fixed number. The output of this step is an ordered set n of all the secondary landmark points on a given femur bone surface.

Segmentation of Rabbit Femur Using ASM

A landmark point set is generated for the femur of each sham-treated rabbit from its μCT images as described above. FIG. 6A shows the mean shape of the rabbit femur bone with a line drawn between every two adjacent landmark. The rabbit femur shape is represented using a total of 1334 3D landmarks points. FIG. 6B shows three variations of femur shapes computed from its shape model equation.

Procrustes analysis is used to align the shapes, and this alignment procedure makes the shape model independent of the size, position, and orientation of the objects. Finally, PCA is applied on the aligned landmark point sets generating a femur shape model, which is essentially a mean femur shape (FIG. 6A) along with an eigenvector and eigenvalue system governing the rabbit femur shape variations.

FIG. 6B illustrates a few instances of femur shape variations computed from its shape model equation. A rabbit femur shape model has been represented using five largest eigenvalues and corresponding eigenvectors. Subsequently, the femur ASM is fitted on the femur surface of a given animal's data using an algorithm, such as the one described in "Active Shape Models—Their Training and Application," *Computer Vision and Image Understanding*, vol. 61, pp. 38-59, 1995. A polyhedral-closed surface is constructed by using a pre-defined adjacency relation among the landmarks (FIG. 6), and a digital volume is computed from this closed surface, which is uniformly eroded to compute the inner femur space.

Mapping Individual Rabbit Femur Shapes Onto MAS

After ASM-based segmentation of μCT images, an ordered set $\{p_1, p_2, \ldots, p_n\}$ of landmarks was obtained for each rabbit femur. Allowing the landmarks $\{q_1, q_2, \ldots, q_n\}$ to denote the mean rabbit femur shape. A transformation function h was computed using the algorithm described above with $p_i$s as the landmarks in the target image, and $\{q_1, q_2, \ldots, q_n\}$ as the landmarks in the template image.

Finally, the transformation function h was applied on the original μCT image of the corresponding rabbit femur. This transformed data is expected to possess a point-by-point registration with the mean femur shape.

Analysis of Regional Bone Architectural Parameters Using AIM

Both material quantity and architectural parameters have been studied and described herein. For material quantity, bone density (TB/TV) was computed and for architectural analysis of TB, digital topological analysis (DTA), which has previously been applied in several clinical and animal studies, was adopted.

Prior to bone density and topological analysis of TB, a bone volume fraction (BVF) map image was computed which provided fractional bone occupancy in each voxel. The (BVF) map image is computed using the down sampled μCT image mapped onto the MAS, allowing f to denote the down sampled image intensity function with nonzero value only over the ROI, allowing $t_B$ to be the bone threshold and $m_B$ to be the mode of bone intensity histogram. Also, X denotes the largest 26-component of thresholded bone voxels. Finally the BVF map $f_{BVF}:C \rightarrow [0,1]$ is computed as follows which is used for computing TB/TV and DTA:

$$f_{BVF}(c) = \begin{cases} 0, & \text{if } c \notin X, \\ 1, & \text{if } f_d(c) > m_B, \\ m_B - f_d(c)/m_B - t_B, & \text{otherwise.} \end{cases} \quad (9)$$

Figure 7:
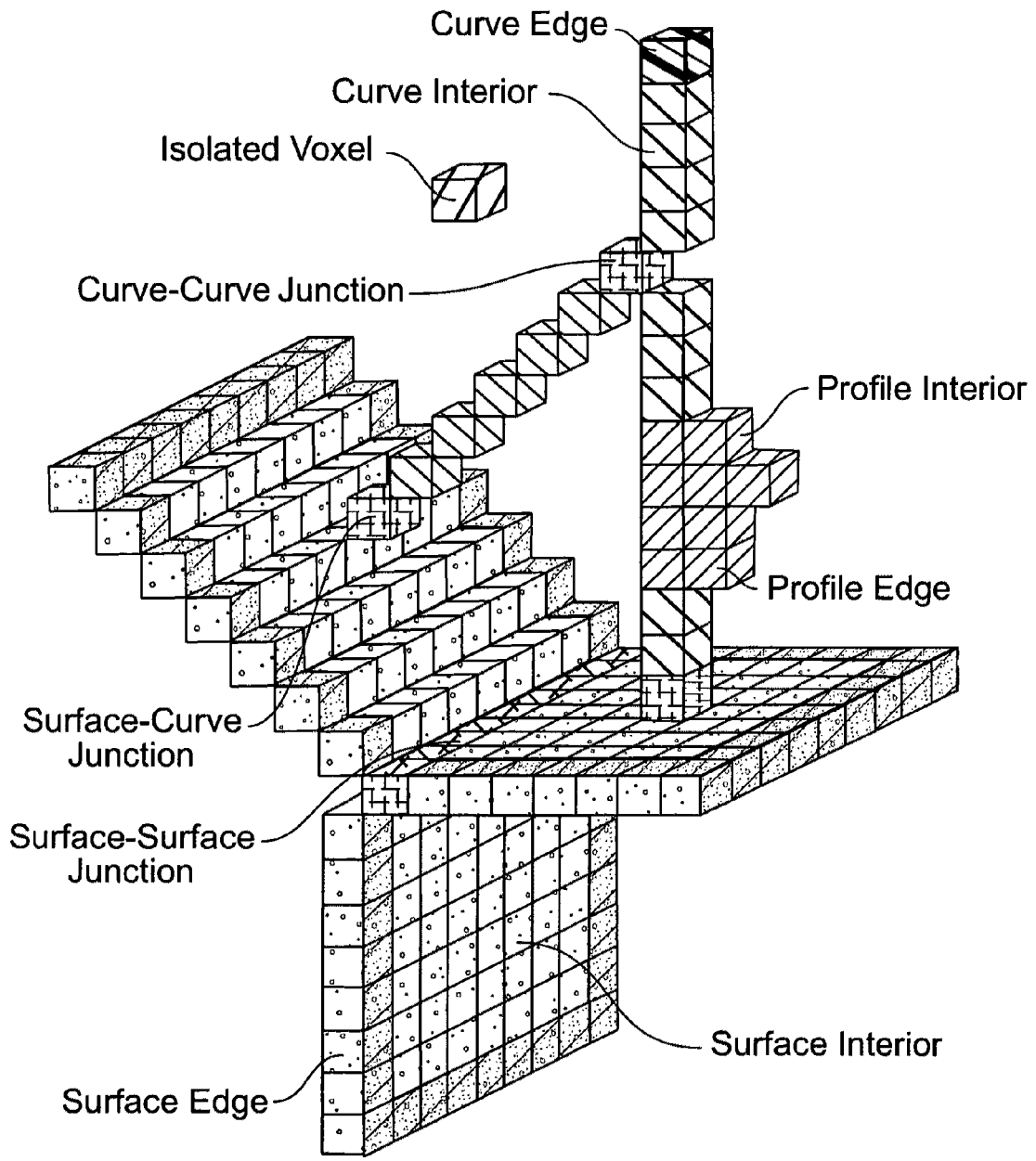
FIG. 7 is a representation of the different topological classes in accordance with the present invention.

FIG. 7 shows different topological classes on a skeletal voxel representation. Digital topological analysis (DTA) is a fully 3D method for analyzing TB topology. The method provides a unique topological class at every TB skeletal voxel. The method may be applied on a 3D object only after its skeletonization which is a topology preserving process that converts a TB into a network single voxel thick surfaces, curves, and their junctions.

DTA is primarily based on analyzing the numbers of objects, tunnels (handles), and cavities in the 3×3×3 neighborhood of a skeletal voxel after its hypothetical deletion i.e., the three numbers, often referred to as local topological numbers, are computed assuming that the central voxel in the 3×3×3 neighborhood is absent.

The key idea may be understood using the following simple observations. For example, a puncture by a needle at a point on a surface always create exactly one tunnel in a sufficiently small neighborhood of the point and this local topological phenomenon is independent of the topology of the entire surface. A similar action creates two objects at point on a curve, multiple tunnels at a junction of multiple surfaces and so on.

However, in a digital space more complications appear and those are solved using a three-pass procedure. In the first pass, only a partial classification may be obtained by analyzing the above-mentioned three local topological numbers. After the second pass, a complete topological classification is accomplished except a few misclassifications, which are solved during the third pass by analyzing the topology of edges and junctions.

The following topological classes as shown in FIG. 7 are recognized by DTA isolated (I), curve-edge (CE), surface-edge (SE), profile-edge (PE), curve-interior (C), surface-interior (S), profile interior (PI), and curve-curve (Ce), surface-curve, and surface-surface junctions. However, for the sake of brevity we have only studied the erosion index (EI) parameter.

Results of the Trial Applications

The steady-state free precession MR imaging of the heart was performed on 25 patients with repaired Tetralogy of Fallot and resultant pulmonic regurgitation. Our study population also included 25 normal subjects. The original 2D long and short axis images were segmented and landmarked using the approach described above.

Figure 8B:
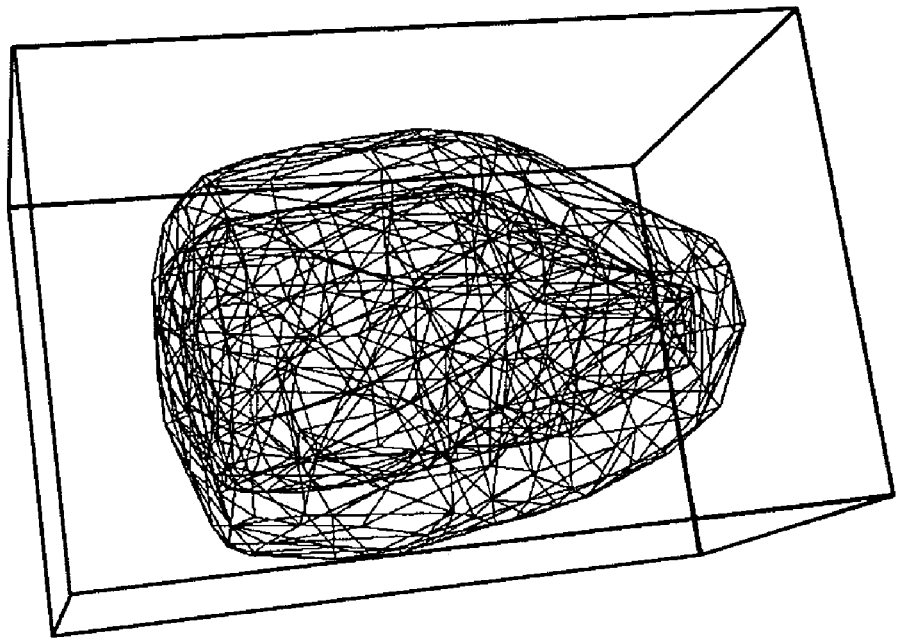
FIGS. 8A-8B are images generated in accordance with the present invention.
Figure 8A:
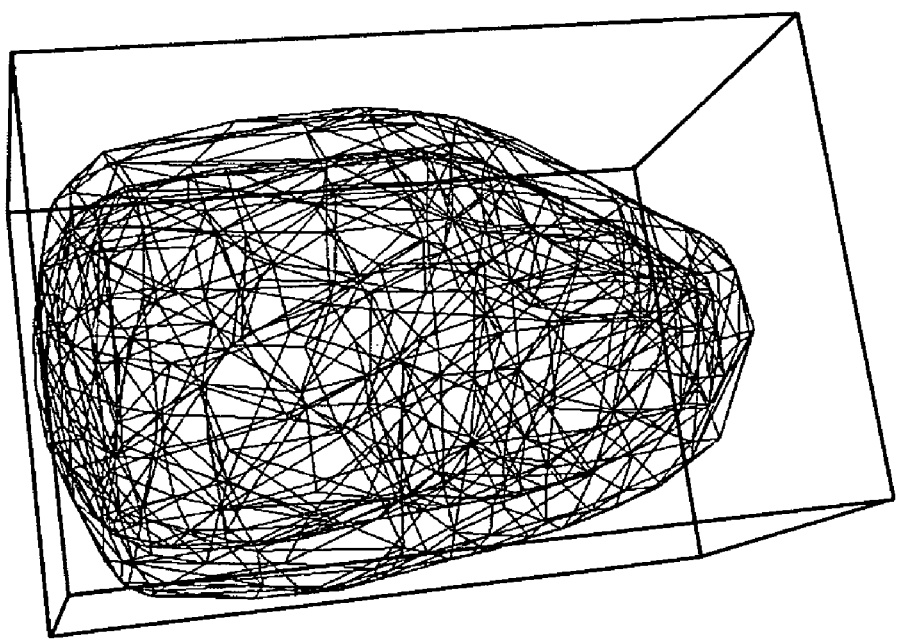

FIG. 8 shows mesh-based landmarked mean model of left cardiac ventricle built from 25 normal and 25 Tetralogy of Fallot subjects at end-diastole (FIG. 8A) and end-systole (FIG. 8B). FIG. 8 shows both endocardium and epicardium surfaces.

In FIG. 8, each mesh node represents a landmark. The landmark-based meshes representing the endo- and epicardial surfaces of the left ventricle as well as the surfaces of the right ventricle were used for the reported regional analyses. Computed regional deformation field was smoothed over second-order neighborhood whose mean radius was 8.11 mm.

Figure 9A:
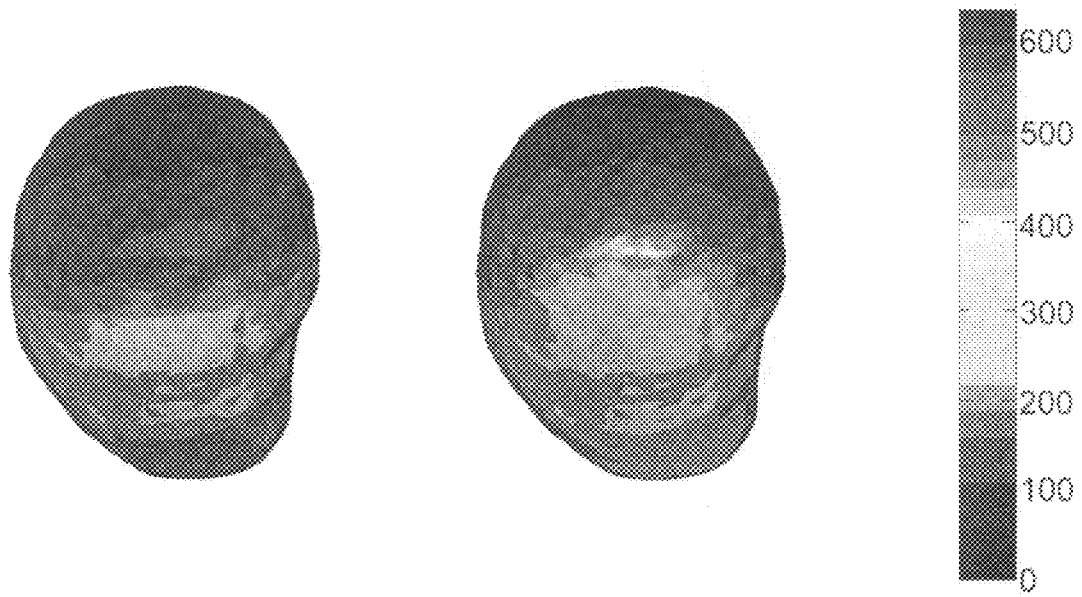
FIGS. 9A-9B are images generated in accordance with the present invention.
Figure 9B:
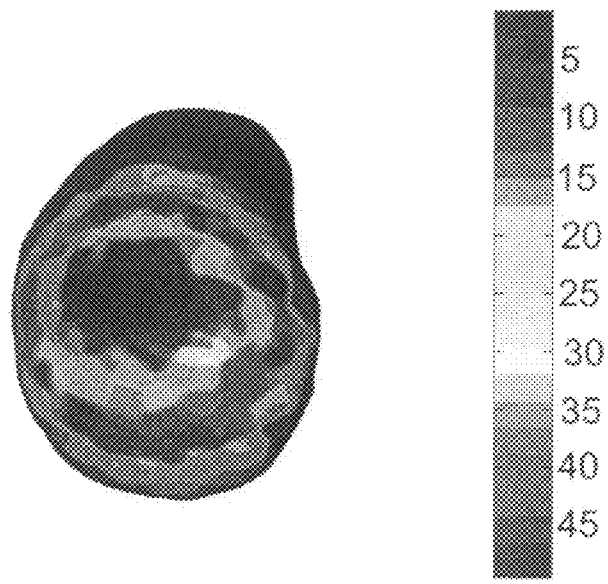

The regional means of local cardiac deformations over epicardial surface for the control (left) and patient groups (right) are illustrated in FIG. 9A. In this figure, each unit in the color scale represents 1/100th of a millimeter. The results of statistical comparison are presented in FIG. 9B where the color at each location, say q, on the epicardial surface depicts the p-value of an unpaired t-test between the cardiac deformations at q computed from the control data sets and the same computed from the patient data set.

For the trabecular bone application, micro-CT data sets of nine sham-treated rabbit femur bones were analyzed. The mean shape and the ASM are illustrated in FIG. 6. The rabbit femur shape is represented using a total of 1334 landmark points. ASM-based segmentation of the femur bone was visually satisfactory for all the nine data sets (see the left and right columns in FIG. 10).

Figure 10:
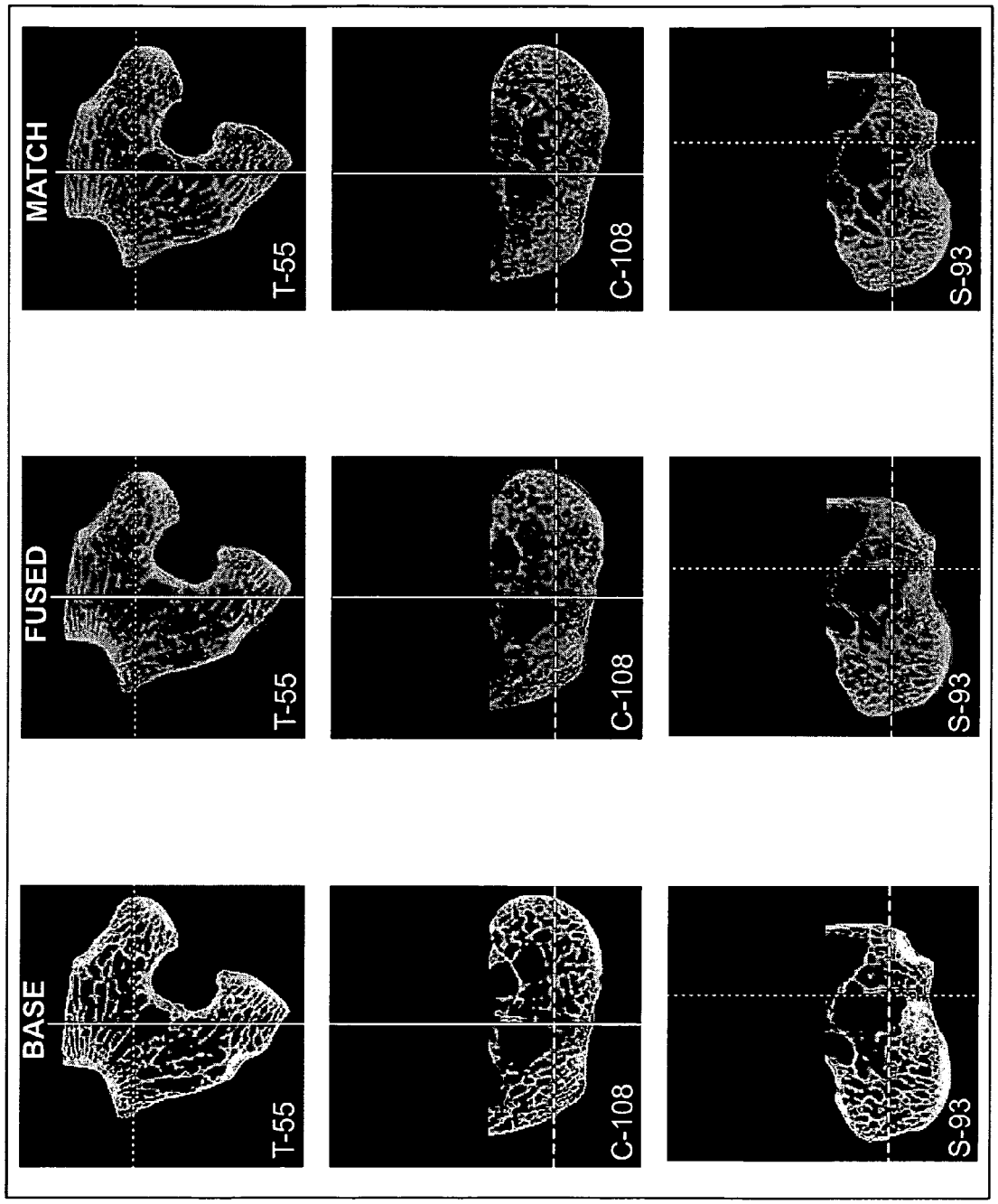
FIG. 10 are images generated in accordance with the present invention.
Figure 11A:
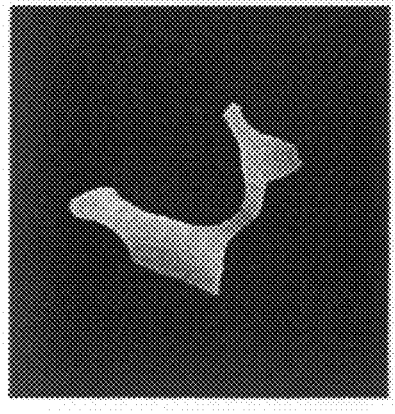
FIGS. 11A-11H are images generated in accordance with the present invention.
Figure 11B:
Figure 11C:
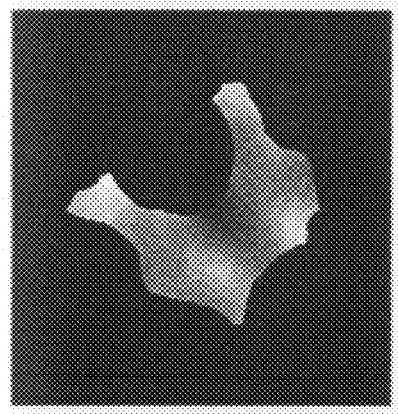
Figure 11D:
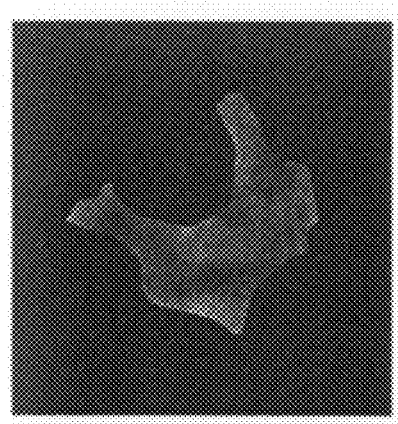
Figure 11E:
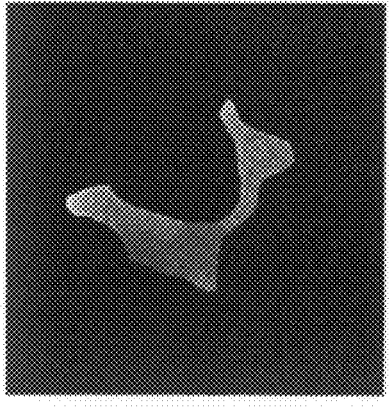
Figure 11F:
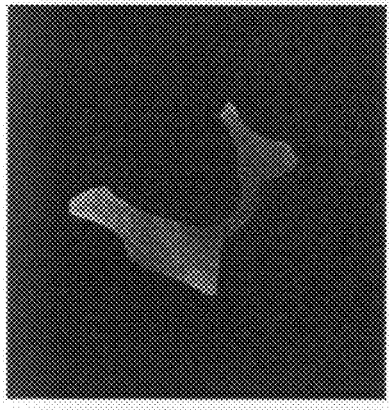
Figure 11G:
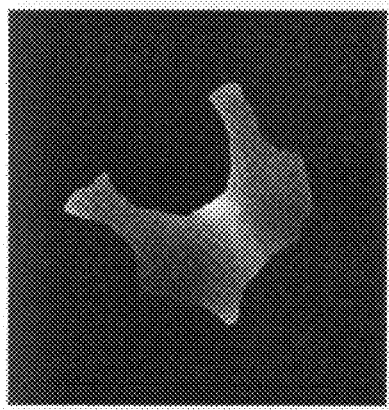
Figure 11H:
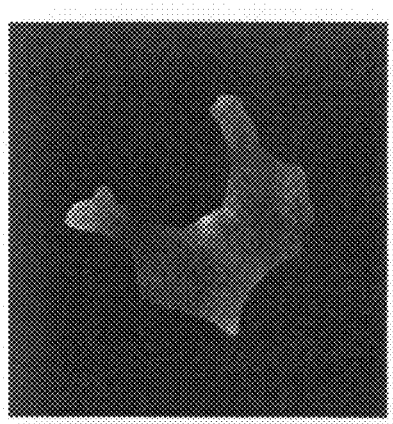

FIG. 10 shows μCT data of two different rabbit femurs after separately warping them onto the mean shape. The rows from top to bottom show axial, coronal, and sagittal views. The left and right columns indicate μCT data of two different rabbit femurs after separately warping them onto the mean shape. The middle column shows a fusion of the μCT images on the left and right columns.

After landmark-based warping of each femur μCT data onto the mean shape, registration of every pair of images were visually inspected by overlaying one on top of other using a graphical interface supported by the Analyze™ software (Mayo Clinic, Rochester, Minn.) as illustrated in FIG. 10. Out of nine registration results, two were discarded due to visually unacceptable registration. Thus, the remaining seven data sets from the control group were used for analysis.

After warping each data sample onto MAS, for each data, at each location the average of each of the TB/TV and EI parameters was computed over a ball neighborhood of radius 10 voxels. This value was considered as the regional value at a given location for a given parameter.

Finally, regional distribution of any parameter is computed as the mean (μ) and standard deviation (σ) of the parameter values at the given location in the seven regionally mapped data sets. The regional values of μ and μ/σ for TB/TV and the erosion index on one slice are illustrated in FIG. 11, which shows the variations of regional distribution of both bone density and structural make-up parameters for the same group of animals.

FIG. 11 shows the regional distribution of TB parameters in control rabbit femur computed using volume-AIM. FIGS. 11A and 11B show distributions of regional mean and mean-std values of TB/TV over a 2D slice of the rabbit femur MAS. FIGS. 11C and 11D are similar to 11A and 11B, but at a different location. FIGS. 11E-11H are the same as 11A-11D but for erosion index E1.

These trial applications included the development of two different types of AIM computational frameworks, one when the data are coming from the surface of an anatomic region, and the other when data are coming from the entire anatomic volume. As described herein, the present invention provides the tool for understanding regional response of disease or treatment at various stages of its progression.

The invention has also been applied to two separate applications. The first application was to compare regional deformation patterns on epicardial surface of cardiac left ventricle for two different groups—control and Tetralogy of Fallot. This experiment was performed on MR images at two time points on cardiac cycle; end-diastole and end-systole. The results have clearly indicated two sites with statistically significant difference in cardiac deformation pattern between the normal and the disease groups.

The other trial application analyzed regional distributions of bone density and architectural parameters in the rabbit femur model. The results demonstrated strong regional differences in both mean and variance values of the bone parameters over the femur region.

While the present disclosure is susceptible to various modifications and alternative forms, specific exemplary embodiments thereof have been shown by way of example in the drawings and have herein been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

What is claimed is:

1. A method for computing regional statistical distribution or characteristics of at least one quantitative measures over a mean anatomic space for at least one predefined population and using this statistical distribution or characteristic to study, research or understand the regional response of a disease or a treatment process and to regionally rate clinical status of patient data from an unknown population for diagnostic purposes, comprising the steps of:
   graphically delineating the landmarks of an anatomical structure to create a mean anatomic space into which patient data can be mapped;
   gathering anatomical structure data from a defined population; and
   mapping the anatomical structure data to the mean anatomic space,
   wherein said step of graphically delineating the landmarks of an anatomical structure to create a mean anatomic space into which patient data can be mapped further comprises the step of computing quantitative indices over the volume of the anatomical structure.

2. The method of claim 1, further comprising the step of using patient data to study and diagnose pathological conditions.

3. The method of claim 1, wherein said anatomical structure comprises any one of the bones of the body.

4. The method of claim 1, wherein said anatomical structure comprises cardiac deformations.

5. The method of claim 1, wherein said graphically delineating the landmarks of an anatomical structure to create a mean anatomic space into which patient data can be mapped is performed manually.

6. The method of claim 1, wherein said gathering anatomical structure data from a given population is done automatically.

7. The method of claim 1, wherein said mapping the data to the mean anatomic space is done automatically.

8. The method of claim 2, wherein said using said patient data to study and diagnose pathological conditions comprises a comparison of patient data to the anatomical structure data mapped to the mean anatomical space.

9. The method of claim 8, wherein said comparison is between a healthy individual and a diseased individual.

10. The method of claim 8, wherein said comparison is between a healthy individual and an unknown individual.

11. The method of claim 8, wherein said comparison is between a first diseased individual and a second diseased individual.

12. The method of claim 8, wherein said comparison is between the same individual over a period of time.

13. The method of claim 1, wherein said gathering anatomical structure data from a given population is performed using medical imaging equipment.

14. The method of claim 13, wherein said medical imaging equipment comprises at least one of a computed tomography scanner, a computed axial tomography scanner, a digital tomosynthesis scanner, a digitally reconstructed radiograph scanner, an electron beam tomography scanner, or an X-ray tomography scanner.

15. A system for computing regional statistical distribution or characteristics of at least one quantitative measures over a mean anatomic space for at least one predefined population and using this statistical distribution or characteristic to study, research or understand the regional response of a disease or a treatment process and to regionally rate clinical status of patient data from an unknown population for diagnostic purposes, comprising:
   a microprocessor;
   a memory coupled to said microprocessor; and
   a program loaded into said memory and accessible by said microprocessor, said program capable of receiving a plurality of landmarks pertaining to an anatomical structure and creating a mean anatomic space based on the plurality of landmarks;
   said program capable of receiving and mapping anatomical structure data from at least one predefined population;
   wherein, once the mean anatomical space is created and the anatomical structure data is mapped to the mean anatomic space and stored in said memory, patient data from an unknown population can be mapped and regional statistical characteristics can be used to assess the clinical status of the patient,
   wherein the mean anatomic space is created by graphically delineating the plurality of landmarks and computing quantitative indices over the volume of the anatomical structure.

16. The system of claim 15, further comprising a communications module and a remote computer, said communications model allowing for the transmission of said mean anatomic space mapped with said anatomical structure data from said memory to said remote computer.

17. The system of claim 16, wherein said patient data from an unknown population is transmitted from said remote computer to said memory.

18. The system of claim 16, wherein said program is transmitted to said remote computer.

19. The method of claim 1, wherein said mapping the data to the mean anatomic space generates a mean anatomic space map.

20. The method of claim 19, wherein said defined population is at least one of a healthy population and a diseased population.

21. The method of claim 20, wherein the mean anatomic space map is generated by mapping the patient data on the mean anatomic space and gathering spatially distributed quantitative measures of the anatomical structure data.

* * * * *